United States Patent [19]

Starnes

[11] Patent Number: 4,526,029

[45] Date of Patent: Jul. 2, 1985

[54] PARTICLE SIZE ANALYSIS

[75] Inventor: Peter E. Starnes, Slough, England

[73] Assignee: Bestobell (U.K.) Limited, Great Britain

[21] Appl. No.: 596,307

[22] Filed: Apr. 3, 1984

[30] Foreign Application Priority Data

Apr. 11, 1983 [GB] United Kingdom ............. 8309716

[51] Int. Cl.³ .......................................... G01N 15/02
[52] U.S. Cl. ............................... 73/61 R; 73/432 PS
[58] Field of Search ............... 73/432 PS, 61 R, 61.4

[56] References Cited

U.S. PATENT DOCUMENTS

| | | | |
|---|---|---|---|
| 3,074,627 | 1/1963 | Goetz | 73/432 PS |
| 3,334,516 | 8/1967 | Cedrone | 73/61 R |
| 3,605,485 | 9/1971 | Badiloch | 73/61 R |
| 3,823,602 | 7/1974 | Anderson | 73/28 |

OTHER PUBLICATIONS

Allen et al., *A New X-Ray Sedimentometer*, Journal of Physics E: Scientific Instruments, vol. 3, Jun. 1970.

*Primary Examiner*—S. Clement Swisher
*Attorney, Agent, or Firm*—Arnold, White & Durkee

[57] ABSTRACT

A method and apparatus for monitoring the fineness of solids in a first suspension of solids in a liquid medium is described. The apparatus comprises a cyclone for separating the first suspension under the influence of a force field into two second suspensions containing respectively solids generally coarser than and generally finer than a predetermined separation size. A constant head device is provided to cause the first and second suspensions to flow through the apparatus. Density measurement means comprising radiation sources, presentation columns, and detectors measure the density of the first suspension and the second suspensions respectively. A computer determines from the measured densities the fineness of solids in the first suspension.

9 Claims, 4 Drawing Figures

PARTICLE SIZE ANALYSIS

This invention relates to the measurement of the fineness of solid materials in liquid suspension, the fineness being conveniently expressed in terms of the proportion of the solid material by weight which is coarser than a given standard sieve mesh. Typical suspensions include pulps and slurries in which the liquid medium is water. The solid material may be for example milled tin ore.

It is known in principle to carry out determinations of fineness on flowing suspensions of solid materials by subjecting the suspension to a force field and measuring the change in concentration of the solid phase across the flow path induced by the force field by radiation absorption means. British Patent Specification No. 1,255,728 discloses a method of on-stream measurement of particle size distribution in a suspension, using the effect of an applied force field to distribute the particles according to their size across a channel in which the stream flows, and measuring the varying concentration of the particles across the flow channel due to this distribution, characterised by the fact that said measurements are made under constant head flow conditions.

According to this latter invention, the force field is applied by causing the suspension to flow thorugh an helical separator which forms part of a continuous single closed flow path in the form of a conduit. Radiation absorption measurements are made on the flow of pulp or slurry at predetermined defined positions with respect to the boundaries of the conduit to determine the change in concentration of the solids phase across said single flow path induced by said force field.

Although the cited invention is sound in principle and capable of achieving the claimed results, in practice it has been found to suffer from a serious defect. The method disclosed is critically dependent upon the maintenance of very close tolerances as regards the dimensions of the separator and flow conduit and also the measurement geometry so that the effect of normal wear over a relatively short operating time is to cause a significant shift in calibration.

In accordance with one aspect of the present invention, a method of monitoring the fineness of solids in a first suspension of solids in a liquid medium flowing under constant head or constant pressure conditions comprises separating the first suspension under the influence of a force field into two flowing second suspensions containing respectively solids generally coarser than and generally finer than a predetermined separation size; measuring the density of the first suspension and the density of at least one of the second suspensions; and determining from the measured densities the fineness of the solids in the first suspension.

In accordance with a second aspect of the present invention, apparatus for monitoring the fineness of solids in a first suspension of solids in a liquid medium comprises separator means for separating the first suspension under the influence of a force field into two second suspensions containing respectively solids generally coarser than and generally finer than a predetermined separation size; flow means incorporating a constant head or constant pressure device for causing the first and second suspensions to flow through the apparatus; density measurement means for measuring the density of the first suspension and at least one of the second suspensions; and fineness determining means for determining from the measured densities the fineness of solids in the first suspension.

With this invention, the flowing first suspension such as a pulp or slurry is separated into two physically separate second or subsidiary flowing suspensions by applying a force field, the force field determining the separation size. Density measurements are then made on the first suspension and on at least one of the second suspensions from which the fineness of the solids present in the first suspension can be determined, the measurements being comparatively insensitive to small changes in apparatus dimensions or measurement geometry.

Although it is sufficient for density measurements to be made on only the first and one of the second suspensions, additional accuracy is obtained by making density measurements on both the second suspensions as well as the first suspension.

It has been found, surprisingly, that the measurement of density is both sufficient and in general more accurate for determing fineness than previous methods which have involved determining mass flow rate. The determination of mass flow rate requires that both density and flow velocity are determined.

The term force field should be interpreted broadly as referring to any force which can separate the first suspension in accordance with particle size. Typically the solids are influenced by forces dependent on their mass and specific surface area (that is surface area per unit weight) and due to their inertial properties. It has been found that the use of such force fields means that the method and apparatus are not susceptable to minor differences in specific gravity. One particularly convenient way to generate the force field is to feed the first suspension to a cyclone. It is thought that the force field causes the solids to react primarily due to their size by virtue of drag effects.

It has been found that a hydrocyclone is more sensitive to differences in particle size than differences in mass. The application of a force field generates two physically separated second flowing suspensions one of which consists essentially of a suspension of solids coarser than the predetermined "separation size" the second of which consists essentially of a suspension of solids finer than the separation size.

Although the invention is particularly applicable to slurries containing solids of the same specific gravity, it may also be used to monitor suspensions containing solids of different specific gravities because the force field acts primarily on particle size (surface area) rather than particle mass.

The step of determining the fineness of the solids may comprise a nomographic method. In such a method, a variety of suspensions of solids of a known fineness are monitored and a graphical representation of the relationship between the fineness of the suspensions and the determined densities is generated. Subsequently, when a suspension of unknown fineness is monitored, the determined densities can be compared with the graphical representation previously generated to determine the fineness of the suspension being monitored. The method and apparatus in accordance with the invention is particularly suitable for use in such a method due to its relative insensitivity to small changes in apparatus dimensions or measurement geometry as mentioned above.

Preferably, the density measurement means provides, at each position where a density measurement is to be carried out, a source of radiation; means for detecting the intensity of radiation passing through the respective suspension; and means for comparing the detected intensity with predetermined intensities due to suspensions of known density to determine the density of the suspension being monitored.

The source of radiation may comprise a source of beta rays but is preferably a source of gamma-rays such as Cs-137.

In practice, the density measurement means may not actually determine densities but instead quantities directly related to the densities.

Conveniently, the fineness determining means comprises a suitably programmed computer or micro-computer. Where the density measurement means is of the form set out above, the computer or micro-computer may provide the means for comparing the detected intensity with predetermined intensities to determine the density of the suspension being measured. Typically, suspensions of known density are fed through the apparatus and the degree of absorption of radiation is determined for these known densities and is stored in a memory connected with the micro-computer or computer. Subsequently, intensities detected during the passage of suspensions of unknown density are compared by the computer or micro-computer with the stored intensities to determine the density of the suspension being measured, the computer or micro-computer being able to interpolate where necessary if the detected intensity does not directly correspond with any known intensity.

In some cases, it may be desirable to extend the method by repeating the monitoring steps on one or both of the second suspensions. Thus, one or both of the second suspensions will then constitute a further first suspension which is separated into two further second suspensions. This process may be repeated as desired. In such a case, the apparatus may further comprise further separator means able to separate the or each further first suspension in accordance with second predetermined separation sizes.

Alternatively, where the first suspension of solids constitutes a sample from a main suspension of solids, then one or more further samples of the main suspension may be taken each constituting a first suspension which is monitored in the same way but is separated into two flowing second suspensions in accordance with different predetermined separation sizes. In this way, a profile of the fineness of solids in the main suspension can be derived.

An example of a method and apparatus in accordance with the present invention will now be described with reference to the accompanying drawings, in which.

Figure 1:
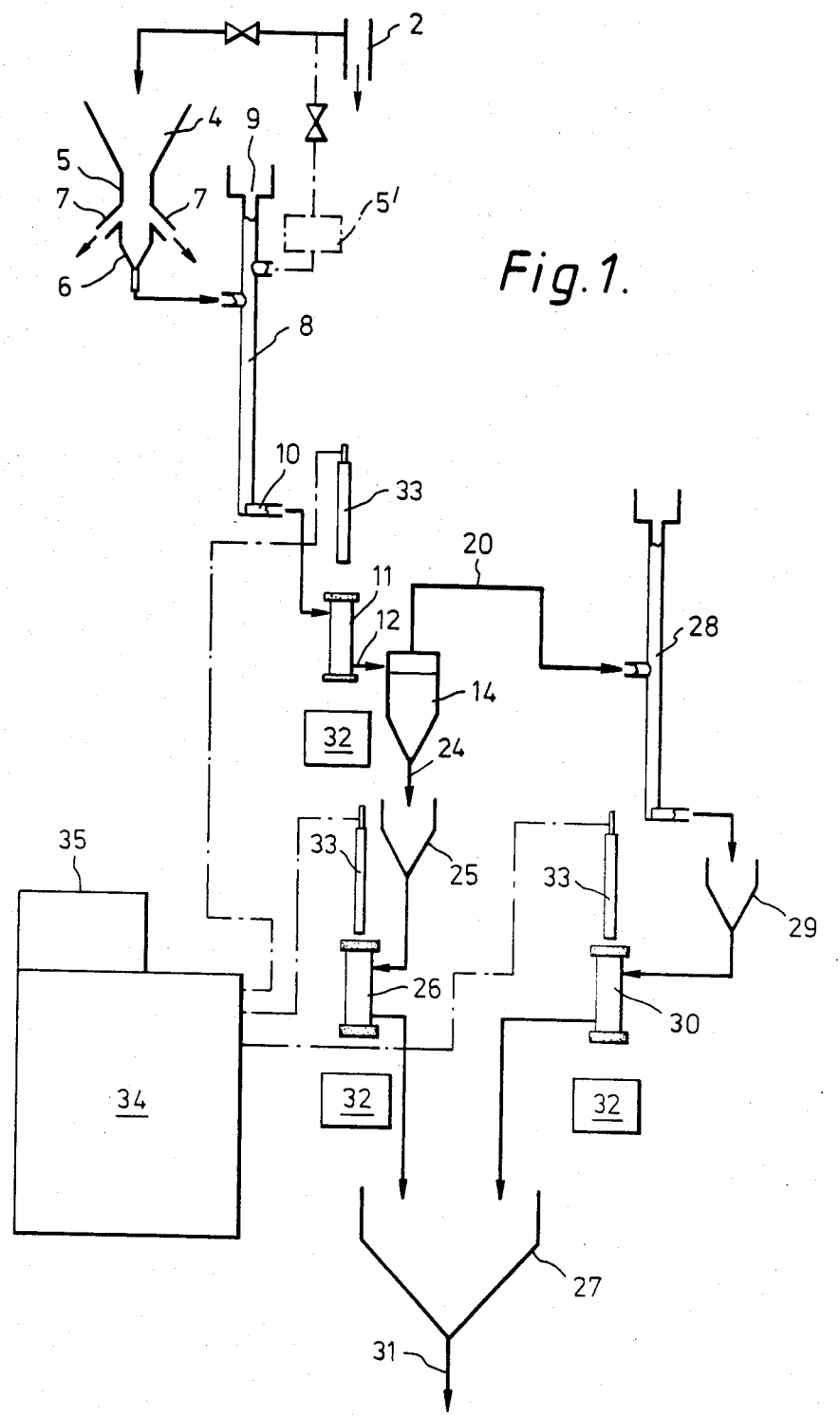
FIG. 1 is a schematic, part flow, diagram of the apparatus.

The apparatus illustrated in FIG. 1 comprises a slurry supply conduit 1 which supplies a sample of a slurry from a main conduit 2 via a control valve 3. The sample of slurry is fed to a conical receiver 4 of a constant head device 5. The constant head device 5 is of known form and has a central outlet 6 and a number of additional outlets 7 (two shown in FIG. 1) so that a constant head is generated. A representative sample (typically 60%) of the slurry is fed at a typical rate of 25 imperial gallons per minute (114 liters per minute) from the central outlet 6 to an inlet of a conventional vortex deairer 8. The vortex deairer 8 comprises a vertically oriented conduit open to the atmosphere at its upper end 9 and connected at its lower end, via a conduit 10, to a gamma-ray presentation column 11 both inlet and outlet conduits being tangential to the main column 11.

Figure 2:
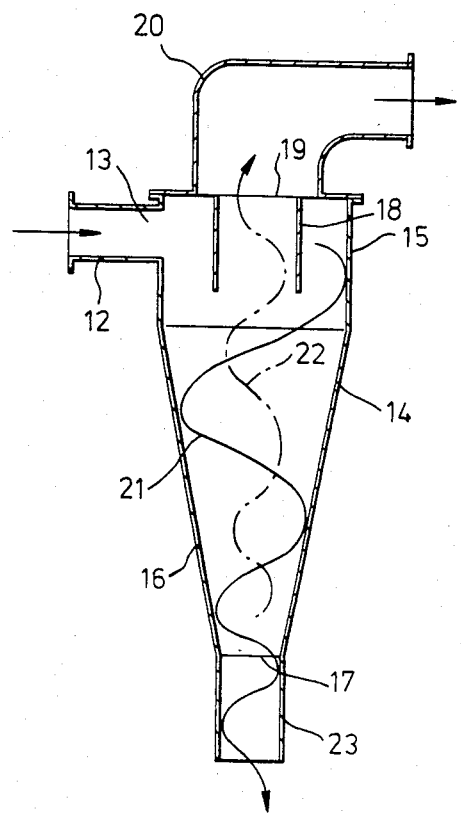
FIG. 2 illustrates an hydrocyclone in more detail.

The gamma-ray presentation column 11 is in communication via a conduit (shown diagrammatically at 12), with an inlet opening 13 of an hydrocyclone 14 (FIG. 2).

The hydrocyclone 14 has an upper cylindrical section 15 and a lower conical section 16 having a downwardly facing outlet opening 17. The upper section 15 includes a cylindrical vortex finder 18 communicating with an upper outlet opening 19 connected with a conduit 20. Typically, for measurement of primary mill products (particle sizes of from 150–200 $\mu$) the internal diameter of the hydrocyclone 14 is in the order of 12 centimeters and all contact surfaces consist of highly wear-resistant cast polyurethane sections. For smaller particle sizes (eg. 10 $\mu$) the hydrocyclone diameter is of the order of 2.5 cm and will be shaped slightly differently as will be apparent to the skilled reader.

In operation, the suspension is fed along the conduit 12 into the inlet opening 13 under pressure caused by the constant head device 5. This, in conjunction with the conical form of the lower section 16 of the hydrocyclone 14, the presence of the vortex finder 18, and the fact that the suspension is fed in a tangental manner into the upper section 15 causes the suspension to describe a helical path within the hydrocyclone. This path results in a redistribution of the solids within the suspension so that those solid particles coarser than a given separation size will pass downwardly through a lower section 16 to the outlet opening 17 as indicated by a line 21 in FIG. 2 will those solid particles having a size generally finer than the separation size will pass upwardly through the vortex finder 18 and the outlet opening 19 into the conduit 20, as indicated by a line 22. Typically, for a given feed material the volume flows, relative densities, and particle size distributions of the "underflow" from the outlet opening 17 and the "overflow" from the outlet opening 19 are determined by the hydrocyclone geometry and the feed input velocity. Of particular significance is the ratio of the bore of a spigot 23 extending from the outlet opening 17 to the bore of the vortex finder 18. It has been found, surprisingly, that for a given design of hydrocyclone operating at a given input head there exists a series of relationships between the feed density, the underflow density, and the particle size characteristics of the original sample. Thus, it is possible to determine the fineness of the original slurry simply by monitoring the density of the incoming suspension and either the "underflow" or the "overflow".

FIG. 1 illustrates, in phantom, an alternative to the constant head device 5 comprising a constant velocity feed, such as a pump 5'.

The underflow from the cyclone 14, which is normally substantially air-free, is fed from the spigot 23 through a conduit 24 to a receiver 25. The receiver 25 can be arranged to deair the underflow if necessary or a further deairer (not shown) could be provided. From the receiver 25, the underflow is fed, under the influence of a head built up in the receiver 25, to a gamma-ray presentation column 26 and from the column 26 to a receiver 27. The overflow is fed along the conduit 20 to a vortex deairer 28 (similar to the deairer 8) and from there via a receiver 29 to a gamma-ray presentation column 30. The presentation column 30 is also in communication with the receiver 27 where the underflow and overflow are recombined. The recombined underflow and overflow are then fed along a conduit 31 either to a dump or back to the main conduit 2 downstream of the sampling position. In an alternative arrangement (not shown) the flows from the presentation columns 26, 30 may be fed to separate constant head devices similar to the constant head device 5 for further measurement.

Each gamma-ray presentation column 11, 26, 30 has a length of about 15 cm and is associated with a source of gamma-rays 32. These sources 32 may typically include a 660 kev gamma ray source such as a suitably shielded preparation of Cs-137 which generates a collimated beam of gamma-rays. The beam of gamma-rays is caused to pass through the respective presentation column and is detected by a conventional radiation detector and associated nucleonics 33. The detectors 33 generate electrical signals corresponding to the intensity of the detected radiation, the electrical signals being fed to a computer 34. Initially water is passed through the apparatus to enable calibration radiation absorption measurements to be made.

In order that the radiation measurements are as accurate as possible, the original slurry is caused to pass through a deairer 8 and the overflow from the cyclone 14 is caused to pass through a deairer 28 prior to passing through the respective presentation columns 11, 30. The vortex deairers 8, 28 remove adventitious air inclusions and/or froth by known principles.

The computer 34 processes the input signals from the detectors 33 in the way described below and is connected to a conventional input/output device 35.

All parts of the apparatus in contact with the flowing suspension are manufactured from a suitable wear-resistance material (as mentioned previously in connection with the hydrocyclone 14), the material preferably being in the form of long-chain polyurethane or other plastic mouldings.

Figure 3:
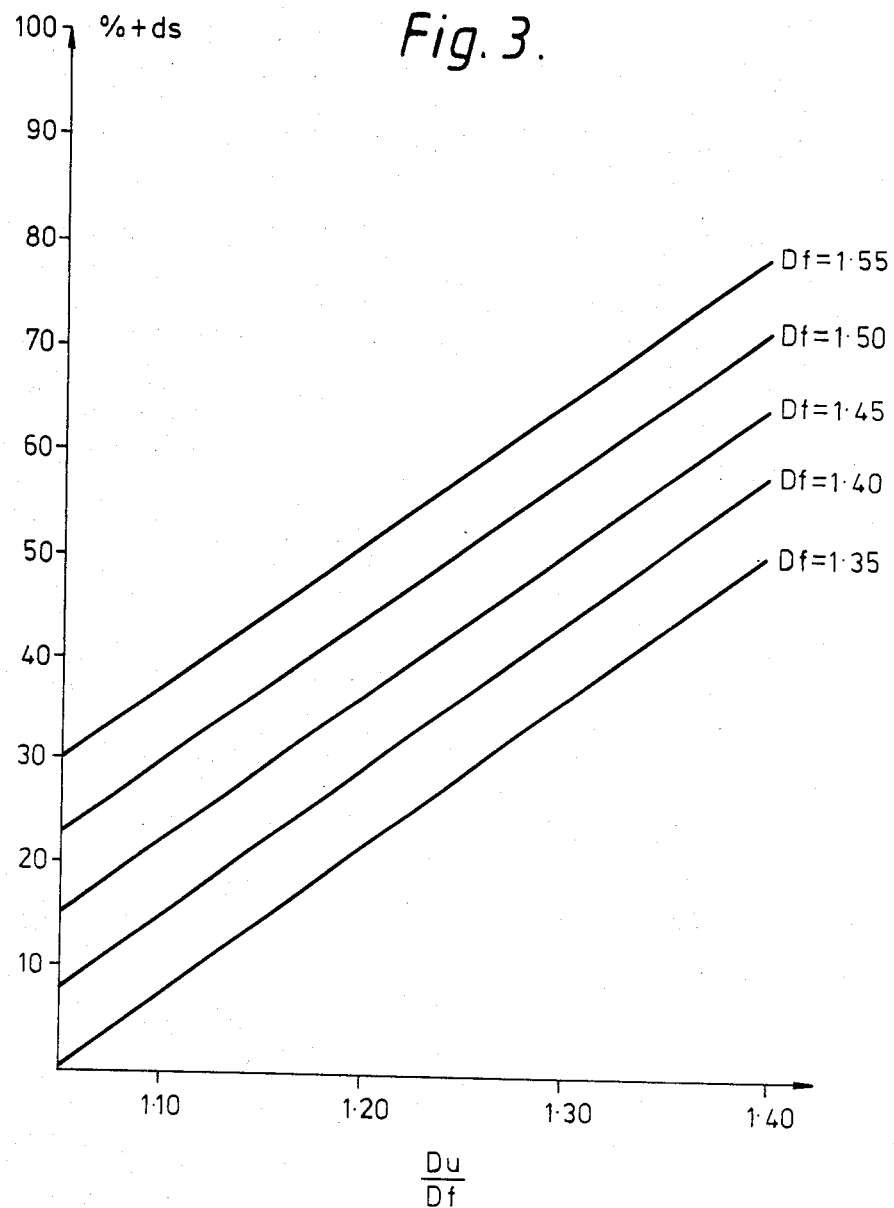
FIG. 3 is an example of a nomogram.

As is mentioned above, for a given design of hydrocyclone 14, operating at a given input head it is found that there exists a series of relationships between the feed density, the underflow density, and the particle size characteristics of the original sample. One such relationship is described by a nomogram of the form shown in FIG. 3 in which $D_f$ represents the density of the feed suspension, $D_u$ the density of the underflow, while %+ds refers to the proportion of the solids present in the original sample coarser than the "effective separation size" ds measured in microns, which is determined by the separator geometry and input head. FIG. 3 illustrates the relationship between %+ds and $D_u/D_f$ for five different values of $D_f$.

The relationship shown in FIG. 3 can be expressed in a mathematical form suitable for computational solution, as follows:

$$\%+ds = K_2 D_f + K_3(D_u/D_f) - K_1$$

where $K_1, K_2,$ and $K_3$ are constants determined in the first instance by making measurements on slurry samples of known fineness characteristics and applying standard correlation procedures.

In one example with a particular hydrocyclone geometry and a particular input feed velocity, $K_1 = 3.358$, $K_2 = 1.44$, and $K_3 = 1.368$ cm$^3$/gm, where $D_f$ is measured in gm/cm$^3$.

Once the apparatus has been calibrated with known samples and the appropriate values for the constants $K_1$, $K_2$, $K_3$ have been fed to the computer 34 via the I/O device 35, the apparatus can then monitor the fineness of unknown slurries, the computer 34 providing an indication of the proportion of solids in the unknown slurries coarser than ds. Auxiliary functions such as "out of limit" commands, mill control signals, and the like can also be executed by the computer via suitable interfaces according to known principles.

From time to time, as programmed, water can be admitted into the apparatus and measurements made, which can be stored in the computer and used as reference standards. In some circumstances, it may also be desirable to introduce water into the apparatus between sample measurements so as to eliminate the possibility of contamination between samples.

Figure 4:
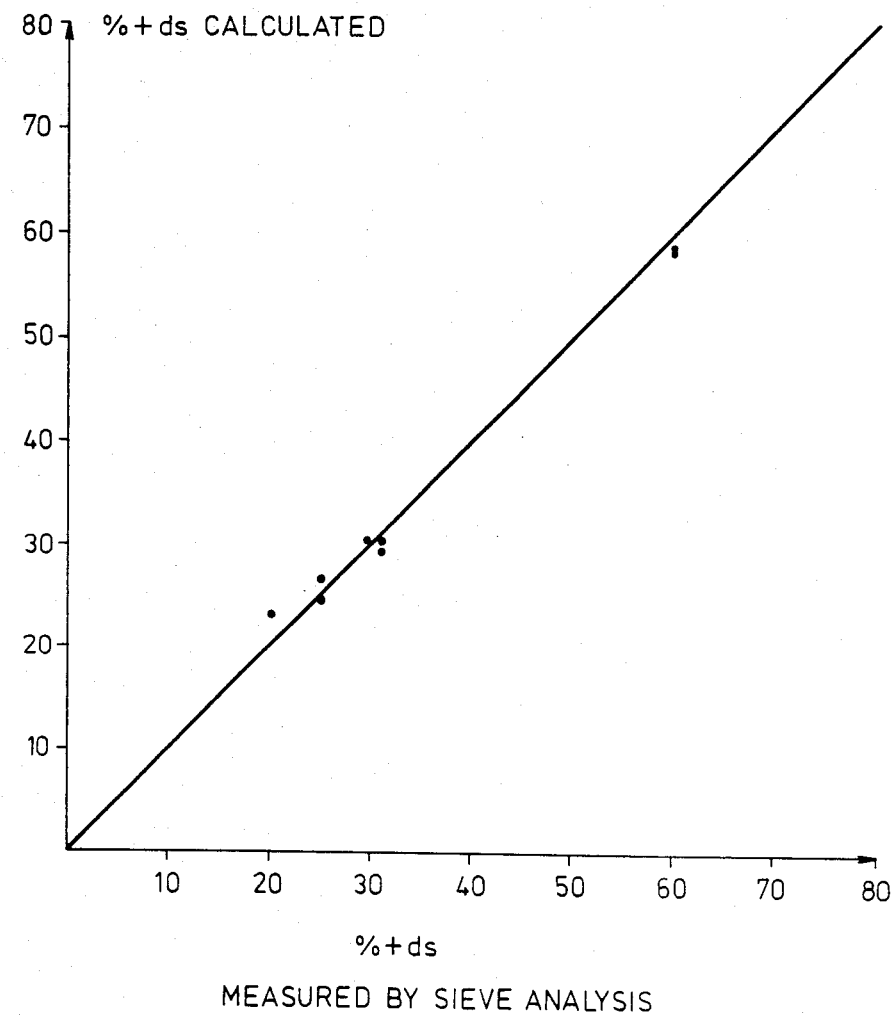
FIG. 4 illustrates graphically the correlation between results obtained by methods in accordance with the invention and results obtained by a conventional sieve analysis.

Typical results obtained using apparatus of the type shown in FIG. 1 and FIG. 2 are illustrated in FIG. 4 which is a correlation plot of the results calculated from measurements carried out by the apparatus against the residues coarser that ds as determined by sieve analysis. It will be seen from FIG. 4 that a close correlation is obtained.

The value of ds can be selected by suitably determining the apparatus design parameters and for a given hydrocyclone 14 can be varied by varying the velocity of the slurry fed into the hydrocyclone 14 or by suitably adjusting the effect of the constant head device 5. Typically, it is possible to obtain a range for ds, the effective separation size, in the order of 10-300 microns by the use of hydrocyclones of appropriate geometries.

I claim:

1. A method of monitoring the fineness of solids in a first suspension of solids in a liquid medium flowing under constant head of constant pressure conditions, the method comprising applying a force field to said first suspension; separating said first suspension under the influence of said force field into two flowing second suspensions containing respectively solids generally coarser than and generally finer than a predetermined separation size; measuring the density of said first suspension and the density of at least one of said second suspensions; and determining from said measured densities said fineness of said solids in said first suspension.

2. A method according to claim 1, wherein the step of determining said fineness of said solids in said first suspension comprises a nomographic method.

3. A method according to claim 1, wherein said fineness of said solids in said first suspension is determined in terms of the proportion by weight coarser than said predetermined separation size in accordance with the following formula:

$$K_2 D_f + K_3(D_u/D_f) - K_1$$

where $D_1$ represents the density of said first suspension, $D_u$ represents the density of one of said second suspensions, and $K_1, K_2,$ and $K_3$ are predetermined constants.

4. A method according to claim 1, wherein, prior to each of said density measurements, adventitious air is removed from the respective suspension.

5. Apparatus for monitoring the fineness of solids in a first suspension of solids in a liquid medium, the apparatus comprising separator means adapted to separate said first suspension under the influence of a field into two second suspensions containing respectively solids generally coarser than and generally finer than a predetermined separation size; flow means incorporating a constant head or constant pressure device adapted to cause said first and second suspensions to flow through said apparatus; density measurement means adapted to measure the density of said first suspension and at least one of said second suspensions; and fineness determining means adapted to determine from said measured densities said fineness of said solids in said first suspension.

6. Apparatus according to claim 5, wherein said density measurement means provides, at each position where a density measurement is to be carried out, a source of radiation; means adapted to detect the intensity of radiation passing through the respective suspension; and means adapted to compare said detected intensity with predetermined intensities due to suspensions of known density to determine the density of the suspension being monitored.

7. Apparatus according to claim 5, wherein said separator means comprises a cyclone.

8. Apparatus according to claim 5, further comprising at least two deairers through respective ones of which said first suspension and said at least one second suspension is adapted to flow before its density is determined by said density measurement means.

9. Apparatus for monitoring the fineness of solids in a first suspension of solids in a liquid medium, the apparatus comprising an hydrocyclone adapted to separate the first suspension under the influence of a force field into two second suspensions containing respectively solids generally coarser and generally finer than a predetermined separation size; a constant head device adapted to cause the first and second suspensions to flow through said apparatus, first density measurement means comprising a first radiation source and a first radiation detector connected to computing means and adapted to measure the density of said first suspension; and second density measurement means comprising a second radiation source and a second radiation detector connected to said computing means and adapted to measure the density of said second suspension containing solids generally coarser than said predetermined separation size, said computing means calculating said fineness of said solids in said first suspension in accordance with the following formula:

$$K_2 D_f + K_3 (D_u/D_f) - K_1$$

where $D_f$ represents the density of said first suspension, $D_u$ represents the density of said second suspension, and $K_1$, $K_2$, and $K_3$ are predetermined constants.

* * * * *